June 13, 1972 H. KOLTKAMP Plant Pat. 3,209
AFRICAN VIOLET
Filed Oct. 7, 1970
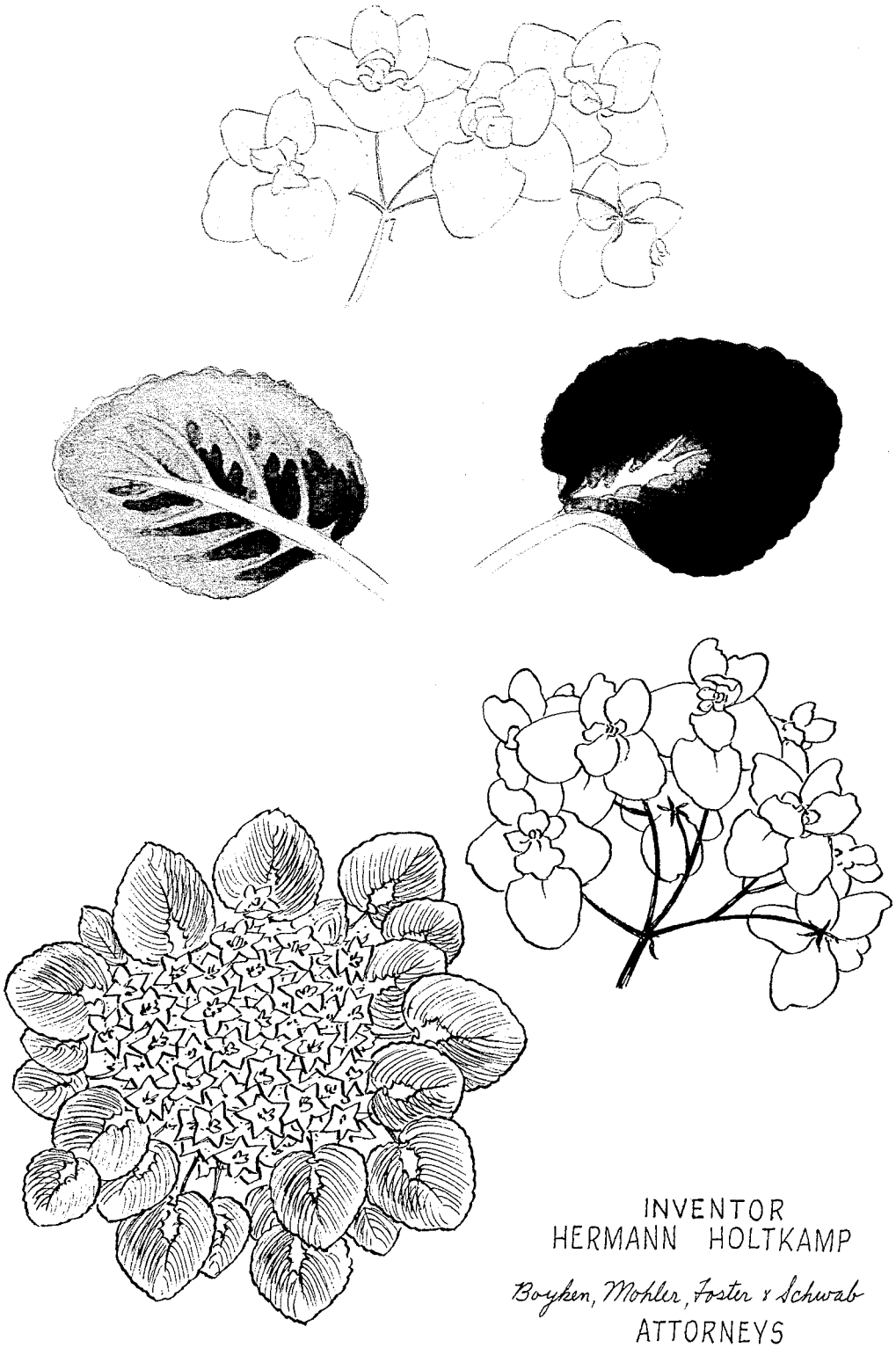
INVENTOR
HERMANN HOLTKAMP
Boyken, Mohler, Foster & Schwab
ATTORNEYS